United States Patent
Hsu et al.

(10) Patent No.: US 8,186,203 B2
(45) Date of Patent: May 29, 2012

(54) DEVICE OF TESTING ROBUSTNESS OF PHOTOVOLTAIC MODULE TERMINAL

(75) Inventors: Yi-Ru Hsu, Kinmen (TW); Yao-Tung Hsu, Taoyuan (TW); Tsung-Te Lin, Kaohsiung (TW); Chii-Neng Ou Yang, Taoyuan (TW)

(73) Assignee: Atomic Energy Council—Institute of Nuclear Energy Research, Taoyuan (TW)

( * ) Notice: Subject to any disclaimer, the term of this patent is extended or adjusted under 35 U.S.C. 154(b) by 387 days.

(21) Appl. No.: 12/637,983

(22) Filed: Dec. 15, 2009

(65) Prior Publication Data
US 2010/0313637 A1    Dec. 16, 2010

(30) Foreign Application Priority Data
Jun. 11, 2009    (TW) ............................... 98119491 A

(51) Int. Cl.
*B23Q 17/20*    (2006.01)
*G01N 3/00*    (2006.01)

(52) U.S. Cl. .......................................................... 73/87
(58) Field of Classification Search ....... 73/78, 760–856
See application file for complete search history.

(56) References Cited

U.S. PATENT DOCUMENTS

| | | | | |
|---|---|---|---|---|
| 4,292,852 | A | * | 10/1981 | Morris ............................ 73/827 |
| 4,924,709 | A | * | 5/1990 | Plyter ............................. 73/829 |
| 6,082,201 | A | * | 7/2000 | Ishikawa ........................ 73/849 |
| 7,895,901 | B2 | * | 3/2011 | Li et al. .......................... 73/818 |

* cited by examiner

*Primary Examiner* — Lisa Caputo
*Assistant Examiner* — Jamel Williams
(74) *Attorney, Agent, or Firm* — Jackson IPG PLLC; Demian K. Jackson

(57) ABSTRACT

A terminal is tested for its robustness. The terminal is for a photovoltaic module. The photovoltaic module is put on a frame unit and is connected with a load unit. The present invention reduces human errors, improves test accuracy and achieves easy operation.

9 Claims, 4 Drawing Sheets

DEVICE OF TESTING ROBUSTNESS OF PHOTOVOLTAIC MODULE TERMINAL

FIELD OF THE INVENTION

The present invention relates to testing robustness of a terminal; more particularly, relates to putting a photovoltaic module on a frame unit and connecting it with a load unit for testing robustness of a test terminal, where the present invention reduces human errors, improves test accuracy and acquires easy operation.

DESCRIPTION OF THE RELATED ART

A general device for test robustness of a terminal of a photovoltaic module usually comprises a rotary structure set with the photovoltaic module; and a weight part set on the test terminal. On testing, two forces are applied manually at two ends of the photovoltaic module simultaneously to rotate the photovoltaic module on the rotary structure and swing the weight part for testing the robustness of the terminal.

Although robustness of a terminal is tested as described above, two forces are required and inconvenience may thus happen. In addition, on rotating the photovoltaic module, test errors may happen owing to unbalanced forces applied manually; and accuracy on test may be thus lost. Hence, the prior art does not fulfill all users' requests on actual use.

SUMMARY OF THE INVENTION

The main purpose of the present invention is to put a photovoltaic module on a frame unit and connecting it with a load unit for testing robustness of a test terminal, where human errors is reduced, test accuracy is improved and easy operation is achieved.

To achieve the above purpose, the present invention is a device of testing robustness of a photovoltaic module terminal, comprising a frame unit, an actuator unit and a load unit, where the frame unit has a platform on top and an angle dial at a side; the actuator unit is set on the frame unit; the actuator unit comprises a drive part, a transmission part, a rotary part, a first switch, and a second switch; the transmission part is connected with the drive part; the rotary part is connected with the transmission part and is movably and correspondingly set at a side of the angle dial; the first switch is electrically connected with the drive part; the second switch is connected with the transmission part; and the load unit is connected with the rotary part of the actuator unit and with a test terminal. Accordingly, a novel device of testing robustness of a photovoltaic module terminal is obtained.

BRIEF DESCRIPTION OF THE DRAWINGS

The present invention will be better understood from the following detailed description of the preferred embodiment according to the present invention, taken in conjunction with the accompanying drawings, in which.

DESCRIPTION OF THE PREFERRED EMBODIMENT

The following description of the preferred embodiment is provided to understand the features and the structures of the present invention.

Figure 1:
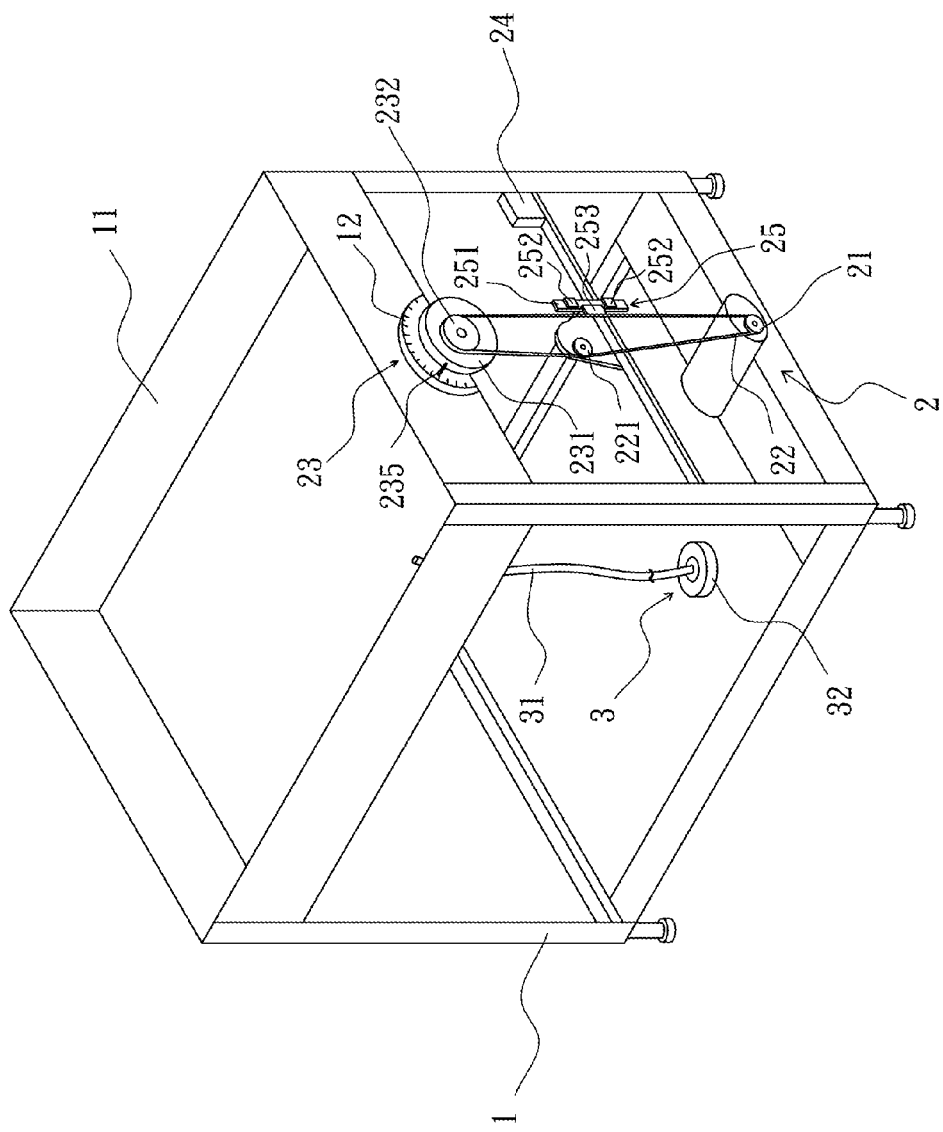
FIG. 1 and FIG. 2 are the first and the second perspective views showing the preferred embodiment according to the present invention.
Figure 2:
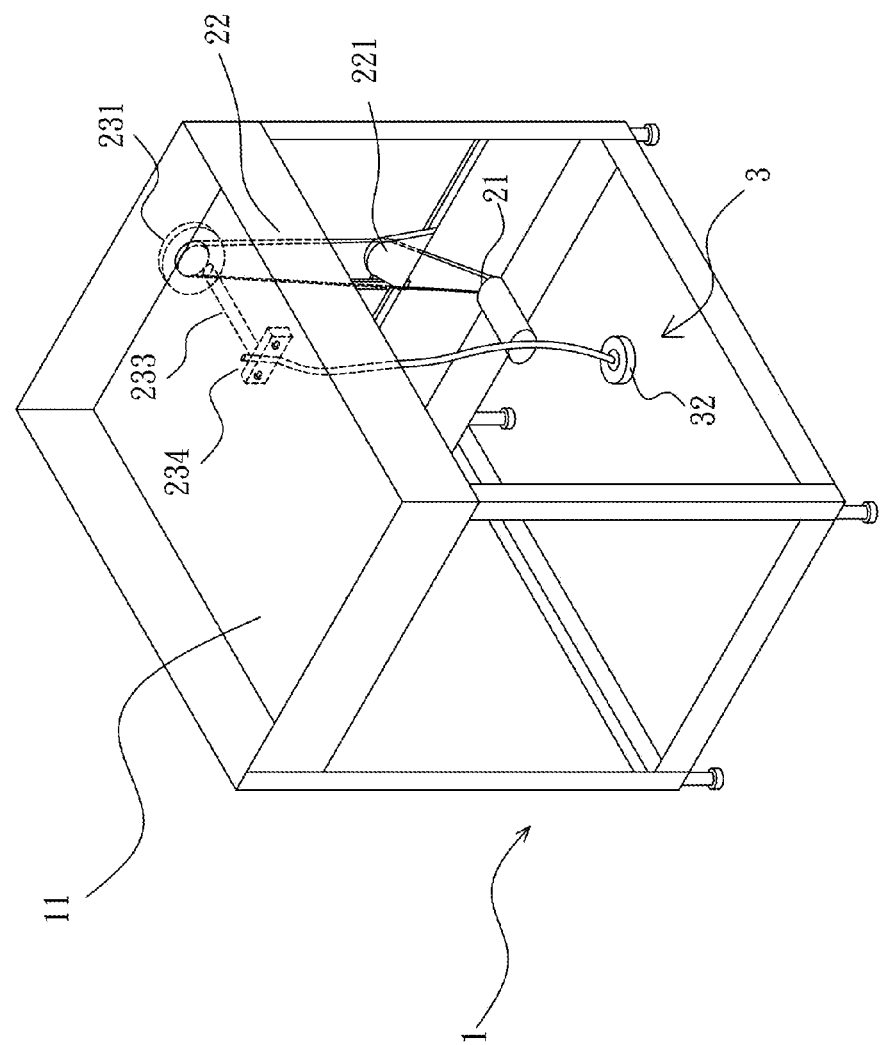

Please refer to FIG. 1 and FIG. 2, which are a first and a second perspective views showing a preferred embodiment according to the present invention. As shown in the figures, the present invention is a device of testing robustness of a photovoltaic module terminal, comprising a frame unit 1, an actuator unit 2 and a load unit.

The frame unit 1 has a platform 11 on top; and an angle dial 12 at a side of the frame unit 1.

The actuator unit 2 is set on the frame unit. The actuator unit 2 comprises a drive part 21; a transmission part 22 connected with the drive part 21; a rotary part 23 connected with the transmission part 22 and movably and correspondingly set at a side of the angle dial 12; a first switch 24 electrically connected with the drive part 21; and a second switch 25 connected with the transmission part. Therein, the drive part 21 is a motor; the transmission part 22 is a chain; the transmission part 22 is further connected with an auxiliary gear 221 set on the frame unit 1; the rotary part 23 comprises a rotating disk 231, a gear 232 and a guide bar 233; the gear 232 is set on a surface of the rotating disk 231; the guide bar 233 is set on the other surface of the rotating disk 231 and is set with two corresponding bearings 234 at an end; the rotating disk 231 has an indicator needle 235 at border corresponding to the angle dial 12; the gear 231 is connected with the transmission part 22; the first switch 24 controls switching-on, switching-off and velocity output of the drive part 21; the second switch 25 is a limit switch; the second switch 25 comprises a fixed platform 251, two limit parts 252 set on the fixed platform 251, and a sliding device 253 between the two limit parts 252 on the fixed platform 251; and, the sliding device 253 is connected with the transmission part 22.

The load unit 3 comprises a wire part 31 connected with the rotary part and a test terminal; and a weight part 32 at an end of the wire part 31. The wire part 32 traverses between the two bearings 234 of the guide bar 233 on the surface of the rotating disk 231. Thus, a novel device of testing robustness of a photovoltaic module terminal is obtained.

Figure 3:
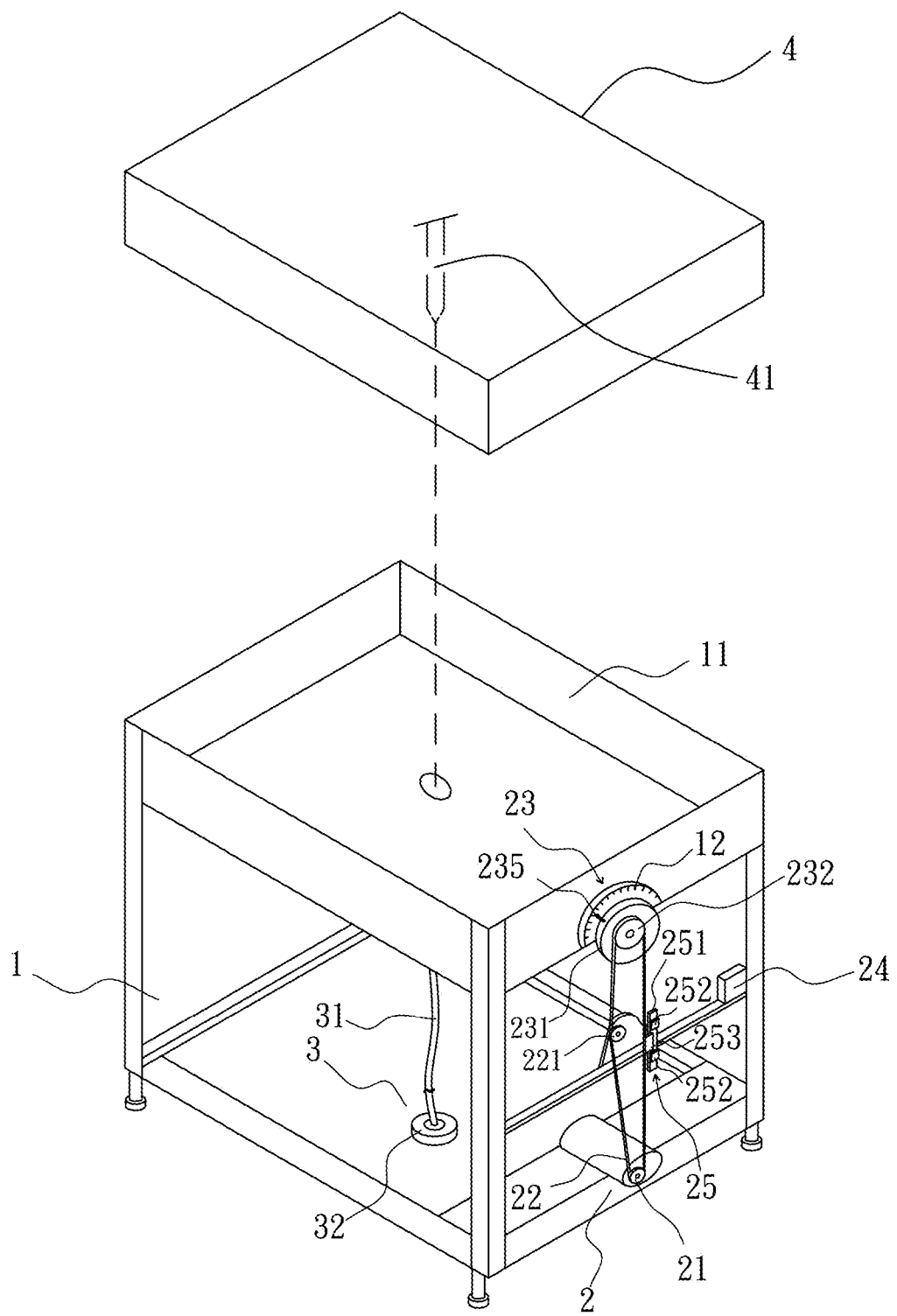
FIG. 3 is the view showing the state of use.
Figure 4:
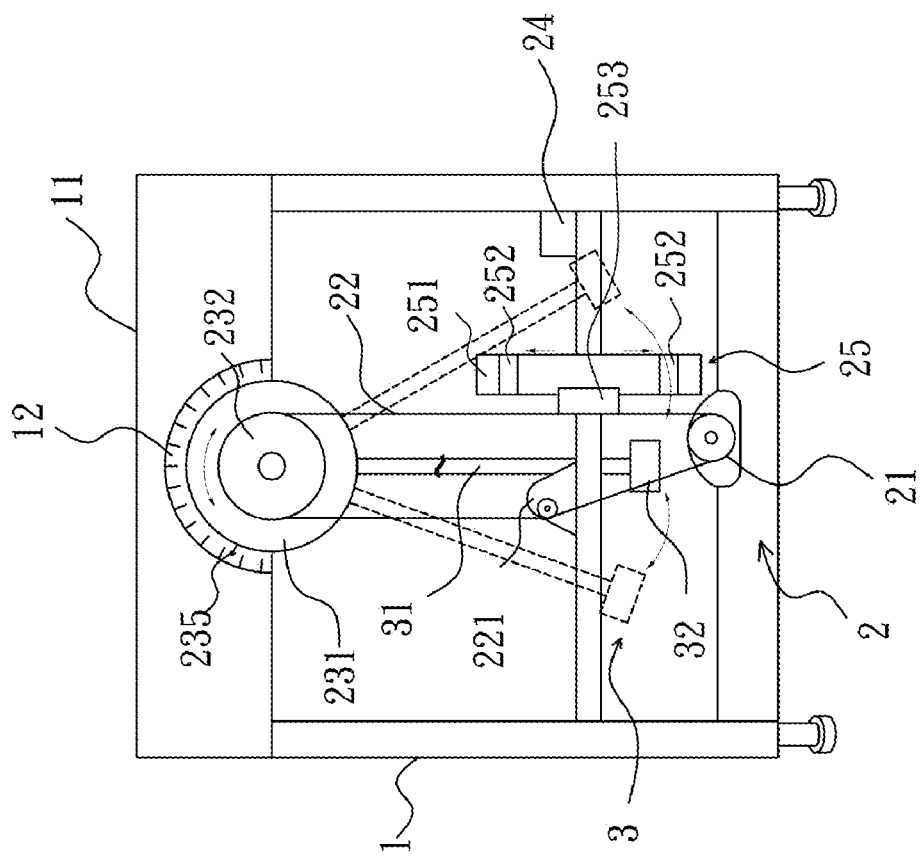
FIG. 4 is the view showing the test case.

Please refer to FIG. 3 and FIG. 4, which are views showing a state of use and a test case. As shown in the figures, a photovoltaic module 4 is set on a platform 11 of a frame unit. A load unit is connected with a test terminal 41 with a wire part 31. A first switch 24 is switched on to rotate a drive part 21 and to control a rotating velocity for driving a transmission part 22 by the drive part 21 to rotate a rotary part 23. When the transmission part 22 moves, an auxiliary gear 221 is used to make smoothly. At the same time, the transmission part 22 makes a gear 232 of the rotary part 23 rotate; and moves a rotating disk 231 and a guide bar 233 by the rotation of the gear 232. Then, the two bearings 234 at an end of the guide bar 233 move the wire part 31 of the load unit 3 to swing a weight part 31 by the wire part 31 and to further pull the test terminal 41 for robustness test. At this time, an indicator needle 235 at border of the rotating disk 231 points to a corresponding scale of an angle dial coordinated with rotation of the rotating disk 231 to acquire a rotating angle of the test terminal 41 from the angle dial 12. Moreover, when the transmission part 22 moves, a sliding device 253 moves at the same time to limit motion of the sliding device 253 between two limit parts 252 on a fixed platform 251; and, the transmission part 22 is thus coordinated with a second switch 25 to control a swinging angle of the weight part 32.

To sum up, the present invention is a device of testing robustness of a photovoltaic module terminal, where a photovoltaic module is set on a frame unit and is connected with a load unit and coordinated with an actuator unit for testing robustness of a test terminal; and, thus, the present invention reduces human errors, improves test accuracy and obtains easy operation.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A device of testing robustness of a photovoltaic module terminal, comprising:
    a frame unit, said frame unit having a platform on top, said frame unit having an angle dial at a side;
    an actuator unit, said actuator unit being positioned on said frame unit, said actuator unit comprising
        a drive part;
        a transmission part, said transmission part being connected with said drive part;
        a rotary part, said rotary part being connected with said transmission part, said rotary part being movably and correspondingly positioned at a side of said angle dial;
        a first switch, said first switch being electrically connected with said drive part; and
        a second switch, said second switch being connected with said transmission part; and
    a load unit, said load unit being connected with said rotary part of said actuator unit and a test terminal.

2. The device according to claim 1,
wherein said drive part is a motor.

3. The device according to claim 1,
wherein said transmission part is a chain and said transmission part is further connected with an auxiliary gear positioned on said frame unit.

4. The device according to claim 1,
wherein said rotary part comprises
    a rotating disk;
    a gear, said gear being positioned on a surface of said rotating disk; and
    a guide bar, said guide bar being positioned on the other surface of said rotating disk, said guide bar being connected with said load unit;
wherein said rotating disk has an indicator needle at border corresponding to said angle dial; and
wherein said gear is connected with said transmission part.

5. The device according to claim 1,
wherein said guide bar has two corresponding bearings at an end.

6. The device according to claim 1,
wherein said first switch controls switching-on, switching-off and velocity output of said drive part.

7. The device according to claim 1,
wherein said second switch is a limit switch;
wherein said second switch comprises a fixed platform;
    two limit parts, said limit parts being movably positioned on said fixed platform; and
    a sliding device, said sliding device being movably positioned on said fixed platform, said sliding device being located between said limit parts; and
    wherein said sliding device is connected with said transmission part.

8. The device according to claim 1,
wherein said load unit comprises
    a wire part, said wire part being connected with said rotary part and said test terminal; and
    a weight part, said weight part being positioned at an end of said wire part.

9. The device according to claim 8,
wherein said wire part traverses between two bearings of a guide bar on a surface of a rotating disk.

* * * * *